(12) United States Patent
Horner et al.

(10) Patent No.: US 11,557,714 B2
(45) Date of Patent: *Jan. 17, 2023

(54) METHOD OF CONSTRUCTING A JAW MEMBER FOR AN END EFFECTOR ASSEMBLY

(71) Applicant: Covidien LP, Mansfield, MA (US)

(72) Inventors: Glenn A. Horner, Boulder, CO (US); Christina A. Oliver, Longmont, CO (US); Kim V. Brandt, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/113,420

(22) Filed: Dec. 7, 2020

(65) Prior Publication Data

US 2021/0091299 A1    Mar. 25, 2021

Related U.S. Application Data

(60) Division of application No. 15/891,532, filed on Feb. 8, 2018, now Pat. No. 10,862,021, which is a division (Continued)

(51) Int. Cl.
*G01R 3/00* (2006.01)
*H01L 41/25* (2013.01)
(Continued)

(52) U.S. Cl.
CPC .......... *H01L 41/25* (2013.01); *A61B 18/1445* (2013.01); *A61B 2018/0063* (2013.01);
(Continued)

(58) Field of Classification Search
CPC ..... A61B 17/0487; A61B 17/28; A61B 17/29; A61B 5/6838; Y10T 74/20666; Y10T 29/42; Y10T 29/49007
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462 Y    9/2009
DE    2415263 A1    10/1975
(Continued)

OTHER PUBLICATIONS

Japanese Office Action dated Aug. 11, 2014, in counterpart JP Application No. 2011-102432; (2 pp).
(Continued)

*Primary Examiner* — Thiem D Phan
(74) *Attorney, Agent, or Firm* — Carter, DeLuca & Farrell LLP

(57) ABSTRACT

An end effector assembly for use with an electrosurgical instrument is provided. The end effector assembly has a pair of opposing jaw members. One or more of the jaw members includes a support base, an electrical jaw lead, and a sealing plate coupled to the electrical jaw lead. The sealing plate has a stainless steel layer and one or more piezo electric sensors. The jaw member also includes an insulative plate disposed between the support base and the sealing plate.

20 Claims, 7 Drawing Sheets

Related U.S. Application Data of application No. 15/055,191, filed on Feb. 26, 2016, now Pat. No. 9,918,783, which is a continuation of application No. 13/893,527, filed on May 14, 2013, now Pat. No. 9,318,691, which is a division of application No. 12/770,369, filed on Apr. 29, 2010, now Pat. No. 8,439,913.

(51) Int. Cl.
*A61B 18/14* (2006.01)
*A61B 18/00* (2006.01)
*A61B 90/00* (2016.01)

(52) U.S. Cl.
CPC ............... *A61B 2018/00083* (2013.01); *A61B 2090/065* (2016.02); *Y10T 29/42* (2015.01); *Y10T 29/49007* (2015.01)

(58) Field of Classification Search
USPC ......... 29/595, 25.35, 825, 829, 846; 606/45, 606/51, 52, 99, 142, 205, 207
See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| 6,017,358 A | 1/2000 | Yoon et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| 7,235,072 B2 | 6/2007 | Sartor et al. |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,491,202 B2 | 2/2009 | Odom et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2* | 8/2010 | Hixson ............... A61B 18/1445 606/49 |
| D627,462 S | 11/2010 | Kingsley |
| D628,289 S | 11/2010 | Romero |
| D628,290 S | 11/2010 | Romero |
| D630,324 S | 1/2011 | Reschke |
| 7,877,853 B2* | 2/2011 | Unger ................ A61B 18/1445 606/49 |
| 7,963,963 B2 | 6/2011 | Francischelli et al. |
| D649,249 S | 11/2011 | Guerra |
| D649,643 S | 11/2011 | Allen, IV et al. |
| 8,080,014 B2 | 12/2011 | Roue et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| D661,394 S | 6/2012 | Romero et al. |
| 8,226,650 B2 | 7/2012 | Kerr |
| 8,251,994 B2 | 8/2012 | McKenna et al. |
| 8,252,626 B2 | 8/2012 | Cho et al. |
| 8,266,783 B2 | 9/2012 | Brandt et al. |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,323,310 B2 | 12/2012 | Kingsley |
| 8,333,765 B2 | 12/2012 | Johnson et al. |
| 8,343,150 B2 | 1/2013 | Artale |
| 8,343,151 B2 | 1/2013 | Siebrecht et al. |
| 8,357,159 B2 | 1/2013 | Romero |
| 8,357,160 B2 | 1/2013 | Odom |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,454,602 B2 | 6/2013 | Kerr et al. |
| 8,469,991 B2 | 6/2013 | Kerr |
| 8,469,992 B2 | 6/2013 | Roy et al. |
| 8,475,474 B2 | 7/2013 | Bombard et al. |
| 8,480,671 B2 | 7/2013 | Mueller |
| 8,491,617 B2 | 7/2013 | Reschke et al. |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,512,371 B2 | 8/2013 | Kerr et al. |
| 8,523,898 B2 | 9/2013 | Bucciaglia et al. |
| 8,529,566 B2 | 9/2013 | Kappus et al. |
| 8,540,712 B2 | 9/2013 | Mueller |
| 8,568,444 B2 | 10/2013 | Cunningham |
| 8,574,230 B2 | 11/2013 | Romero |
| 8,591,511 B2 | 11/2013 | Romero |
| 8,597,296 B2 | 12/2013 | Lawes et al. |
| 8,668,691 B2 | 3/2014 | Heard |
| 8,679,140 B2 | 3/2014 | Butcher |
| RE44,834 E | 4/2014 | Dumbauld et al. |
| 8,696,667 B2 | 4/2014 | Guerra et al. |
| 8,747,413 B2 | 6/2014 | Dycus |
| 8,752,264 B2 | 6/2014 | Ackley et al. |
| 8,764,749 B2 | 7/2014 | McKenna et al. |
| 8,858,554 B2 | 10/2014 | Kerr et al. |
| 8,887,373 B2 | 11/2014 | Brandt et al. |
| 8,920,461 B2 | 12/2014 | Unger et al. |
| 8,939,975 B2 | 1/2015 | Twomey et al. |
| 8,961,514 B2 | 2/2015 | Garrison |
| 8,968,298 B2 | 3/2015 | Twomey |
| 8,968,308 B2 | 3/2015 | Horner et al. |
| 8,968,311 B2 | 3/2015 | Allen, IV et al. |
| 8,968,313 B2 | 3/2015 | Larson |

(56) References Cited

U.S. PATENT DOCUMENTS

| | | |
|---|---|---|
| 9,011,435 B2 | 4/2015 | Brandt et al. |
| 9,011,436 B2 | 4/2015 | Garrison |
| 9,318,691 B2 | 4/2016 | Horner et al. |
| 9,918,783 B2 | 3/2018 | Horner et al. |
| 2004/0230262 A1 | 11/2004 | Sartor et al. |
| 2006/0224158 A1 | 10/2006 | Odom et al. |
| 2007/0062017 A1 | 3/2007 | Dycus et al. |
| 2008/0319442 A1 | 12/2008 | Unger et al. |
| 2009/0149853 A1 | 6/2009 | Shields et al. |
| 2009/0204114 A1 | 8/2009 | Odom |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0249769 A1 | 9/2010 | Nau, Jr. et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt et al. |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0073246 A1 | 3/2011 | Brandt et al. |
| 2011/0073594 A1 | 3/2011 | Bonn |
| 2011/0077648 A1 | 3/2011 | Lee et al. |
| 2011/0118736 A1 | 5/2011 | Harper et al. |
| 2011/0190653 A1 | 8/2011 | Harper et al. |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301600 A1 | 12/2011 | Garrison et al. |
| 2011/0301604 A1 | 12/2011 | Horner et al. |
| 2011/0319886 A1 | 12/2011 | Chojin et al. |
| 2012/0172873 A1 | 7/2012 | Artale et al. |
| 2012/0172925 A1 | 7/2012 | Dumbauld et al. |
| 2012/0296371 A1 | 11/2012 | Kappus et al. |
| 2012/0303026 A1 | 11/2012 | Dycus et al. |
| 2012/0310240 A1 | 12/2012 | Olson et al. |
| 2013/0026053 A1 | 1/2013 | Chowaniec et al. |
| 2013/0030432 A1 | 1/2013 | Garrison et al. |
| 2013/0035688 A1 | 2/2013 | Kerr et al. |
| 2013/0103041 A1 | 4/2013 | Regadas |
| 2013/0116690 A1 | 5/2013 | Unger |
| 2013/0190753 A1 | 7/2013 | Garrison et al. |
| 2013/0190755 A1 | 7/2013 | Deborski et al. |
| 2013/0190760 A1 | 7/2013 | Allen, IV et al. |
| 2013/0197503 A1 | 8/2013 | Orszulak |
| 2013/0218198 A1 | 8/2013 | Larson et al. |
| 2013/0218199 A1 | 8/2013 | Kerr et al. |
| 2013/0219691 A1 | 8/2013 | Reschke |
| 2013/0226226 A1 | 8/2013 | Garrison et al. |
| 2013/0231662 A1 | 9/2013 | Kappus et al. |
| 2013/0238017 A1 | 9/2013 | Kerr et al. |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0274736 A1 | 10/2013 | Garrison |
| 2013/0282010 A1 | 10/2013 | Mckenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 3612646 A1 | 4/1987 |
| DE | 8712328 U1 | 3/1988 |
| DE | 04303882 02 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1159926 A2 | 3/2003 |
| EP | 1707143 A1 | 10/2006 |
| EP | 1810628 A1 | 7/2007 |
| EP | 1946715 | 7/2008 |
| EP | 1990019 | 11/2008 |
| JP | 61501068 | 9/1984 |
| JP | 1147150 A | 6/1989 |
| JP | 65502328 | 3/1992 |
| JP | 55106 | 1/1993 |
| JP | 0540112 | 2/1993 |
| JP | H0540112 A | 2/1993 |
| JP | 0006030945 | 2/1994 |
| JP | 6121797 A | 5/1994 |
| JP | 6285078 A | 10/1994 |
| JP | 06343644 | 12/1994 |
| JP | 6511401 | 12/1994 |
| JP | H06343644 A | 12/1994 |
| JP | 07265328 | 10/1995 |
| JP | H07265328 A | 10/1995 |
| JP | 08056955 | 3/1996 |
| JP | H0856955 A | 3/1996 |
| JP | 08252263 A | 10/1996 |
| JP | 8289895 A | 11/1996 |
| JP | H08289895 | 11/1996 |
| JP | 8317934 A | 12/1996 |
| JP | 8317936 A | 12/1996 |
| JP | H08317934 | 12/1996 |
| JP | H08317936 | 12/1996 |
| JP | 910223 A | 1/1997 |
| JP | 09000538 A | 1/1997 |
| JP | H0910223 A | 1/1997 |

(56) References Cited

FOREIGN PATENT DOCUMENTS

| | | |
|---|---|---|
| JP | 9122138 A | 5/1997 |
| JP | 0010000195 A | 1/1998 |
| JP | H1024051 A | 1/1998 |
| JP | 10155798 A | 6/1998 |
| JP | F10155798 A | 6/1998 |
| JP | H1147150 A | 2/1999 |
| JP | 11070124 A | 3/1999 |
| JP | H1170124 A | 3/1999 |
| JP | 11169381 A | 6/1999 |
| JP | H11169381 | 6/1999 |
| JP | 11192238 A | 7/1999 |
| JP | H11192238 | 7/1999 |
| JP | 11244298 | 9/1999 |
| JP | H11244298 A | 9/1999 |
| JP | 2000102545 A | 4/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | H0630945 B2 | 11/2016 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 03090630 A3 | 4/2004 |
| WO | 2004/073753 A2 | 9/2004 |
| WO | 2004073490 A2 | 9/2004 |
| WO | 2006021269 A1 | 3/2006 |
| WO | 2005110264 A2 | 4/2006 |
| WO | 2008040483 A1 | 4/2008 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Dec. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 39, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al., "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul. 8, 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Canadian Office Action dated Oct. 7, 2016, issued in Canadian Application No. 2,738,311.
Chung et al., "Clinical Experience of Sutureless Closed Hemontoidectomy with LigaSure"; Diseases of the Colon & Rectum vol. 46, No. 1 Jan. 2003.
Crawford et al. "Use of the LigaSure Vessel Sealing System in Urologic Cancer Surgery"; Grand Rounds in Urology 1999 vol. 1 Issue 4 pp. 10-17.

\* cited by examiner

METHOD OF CONSTRUCTING A JAW MEMBER FOR AN END EFFECTOR ASSEMBLY

CROSS-REFERENCE TO RELATED APPLICATIONS

The present application is a divisional of U.S. patent application Ser. No. 15/891,532, filed Feb. 8, 2018, which is a divisional of U.S. patent application Ser. No. 15/055,191, filed Feb. 26, 2016, now U.S. Pat. No. 9,918,783, which is a continuation of U.S. patent application Ser. No. 13/893,527, filed May 14, 2013, now, U.S. Pat. No. 9,318,691, which is a divisional of U.S. patent application Ser. No. 12/770,369, filed Apr. 29, 2010, now U.S. Pat. No. 8,439,913. The entire contents of each of the above applications are incorporated herein by reference.

BACKGROUND

1. Technical Field

The present disclosure relates to an electrosurgical instrument and method for sealing tissue. More particularly, the present disclosure relates to an electrosurgical tool including opposing jaw members having pressure sensors for determining a seal pressure and controlling operation of the electrosurgical tool based on the determined seal pressure.

2. Background of the Related Art

Electrosurgical forceps utilize mechanical clamping action along with electrical energy to effect hemostasis on the clamped tissue. The forceps (open, laparoscopic or endoscopic) include electrosurgical sealing plates which apply the electrosurgical energy to the clamped tissue. By controlling the intensity, frequency and duration of the electrosurgical energy applied through the sealing plates to the tissue, the surgeon can coagulate, cauterize, and/or seal tissue.

Since tissue sealing procedures involve more than simply cauterizing tissue and blood, to create an effective seal the procedures involve precise control of a variety of factors. In order to affect a proper seal in vessels or tissue, it has been determined that two predominant mechanical parameters should be accurately controlled: the pressure applied to the tissue; and the gap distance between the electrodes (i.e., distance between opposing jaw members when closed about tissue).

Numerous electrosurgical instruments have been proposed in the past for various endoscopic surgical procedures. However, most of these instruments cauterize or coagulate tissue and do not allow the sufficiently strong tissue fusion of all tissue types. Consequentially, many of the existing instruments generally rely on clamping pressure alone to procure proper sealing thickness and are often not designed to take into account the seal pressure and applying energy to seal the tissue either sinusoidally or based on feedback from the tissue or properties of the device.

SUMMARY

In an embodiment of the present disclosure, an end effector assembly including a pair of opposing jaw members is provided. One or more of the jaw members includes a support base, an electrical jaw lead, and a sealing plate coupled to the electrical jaw lead. The sealing plate has a stainless steel layer and one or more piezo electric sensors. The jaw member also includes an insulative plate disposed between the support base and the sealing plate.

The insulative plate is a flex circuit having a plastic substrate and a circuit trace having one or more contacts coupled thereto. The one or more contacts are coupled to one or more piezo electric sensors. The contact may be operatively coupled to a controller via a contact trace.

In another embodiment of the present disclosure, an electrosurgical instrument for sealing tissue is provided. The electrosurgical instrument may include a housing having at least one shaft that extends therefrom, a handle assembly operably coupled to the housing, a rotating assembly operably coupled to and configured to rotate the at least one shaft and an end effector assembly disposed at a distal end of the at least one shaft including a pair of opposing jaw members. One or more of the jaw members includes a support base, an electrical jaw lead, and a sealing plate coupled to the electrical jaw lead. The sealing plate has a stainless steel layer and one or more piezo electric sensors. The jaw member also includes an insulative plate disposed between the support base and the sealing plate.

The insulative plate is a flex circuit having a plastic substrate and a circuit trace having one or more contacts coupled thereto. The one or more contacts are coupled to one or more piezo electric sensors. The contact may be operatively coupled to a controller via a contact trace.

In yet another embodiment, a method of constructing a jaw member for an end effector assembly is provided. The method includes creating a seal plate by shaping a stainless steel layer into a seal plate, applying a first mask to the stainless steel layer, wherein the first mask exposes a portion of the stainless steel layer, etching the exposed portion of stainless steel layer to create one or more holes in the stainless steel layer and removing the mask. An insulative plate is also created by providing a plastic substrate, adhering a conductive layer to the plastic substrate, applying a second mask to the conductive layer, wherein the second mask exposes a portion of the conductive layer to outline one or more circuit traces and one or more contacts, etching the exposed portion the conductive layer, and removing the mask. A support base is provided and the insulative plate is attached to the support base and the seal plate is attached on top of the insulative plate so that the one or more holes of the seal plate overlaps the one or more contacts of the insulative plate. A piezo electric sensor is coupled to the at least one contact of the insulative plate. The piezo electric sensor is disposed in the one or more holes of the seal plate.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
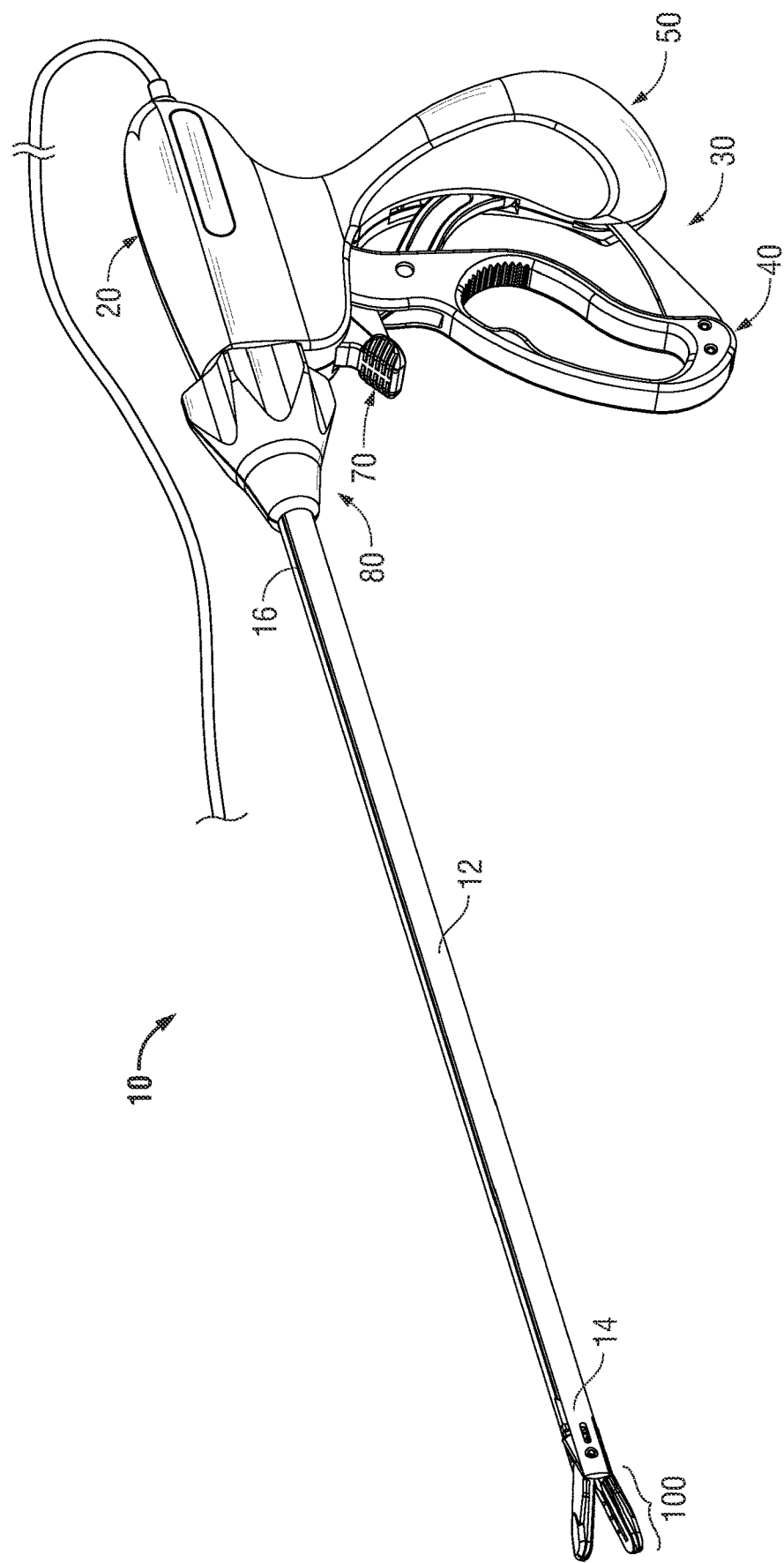
FIG. 1 is a perspective view of an endoscopic bipolar forceps in accordance with an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of embodiments described herein.

As described in more detail below with reference to the accompanying figures, the present disclosure is directed the use of piezo electric sensors in a vessel sealing procedure. More specifically, piezo electric sensors are used instead of conventional ceramic stop members. The piezo electric sensors provide a seal pressure to a controller that adjusts the closure pressure of the jaw members according to open loop or closed loop feedback mechanisms. By using piezo electric sensors instead of stop members, jaw members may be made smaller as well as provide better controlled sealing of certain tissue types or new tissue types.

Turning to FIG. 1, an instrument generally identified as forceps 10 is for use with various surgical procedures and includes a housing 20, a handle assembly 30, a rotating assembly 80, a trigger assembly 70, and an end effector assembly 100 that mutually cooperate to grasp, seal, and divide tubular vessels and vascular tissues. Forceps 10 includes a shaft 12 that has a distal end 16 dimensioned to mechanically engage the end effector assembly 100 and a proximal end 14 that mechanically engages the housing 20. The end effector assembly 100 includes opposing jaw members 110 and 120, which cooperate to effectively grasp tissue for sealing purposes. The end effector assembly 100 is a bilateral assembly, i.e., both jaw members 110 and 120 pivot relative to one another about a pivot pin 95. Unilateral jaw assemblies may also be contemplated. The jaw members 110 and 120 are curved to facilitate manipulation of tissue and to provide better "line of sight" for accessing targeted tissues.

Examples of forceps are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156, 846) entitled "VESSEL SEALER AND DIVIDER FOR USE WITH SMALL TROCARS AND CANNULAS.

Figure 2:
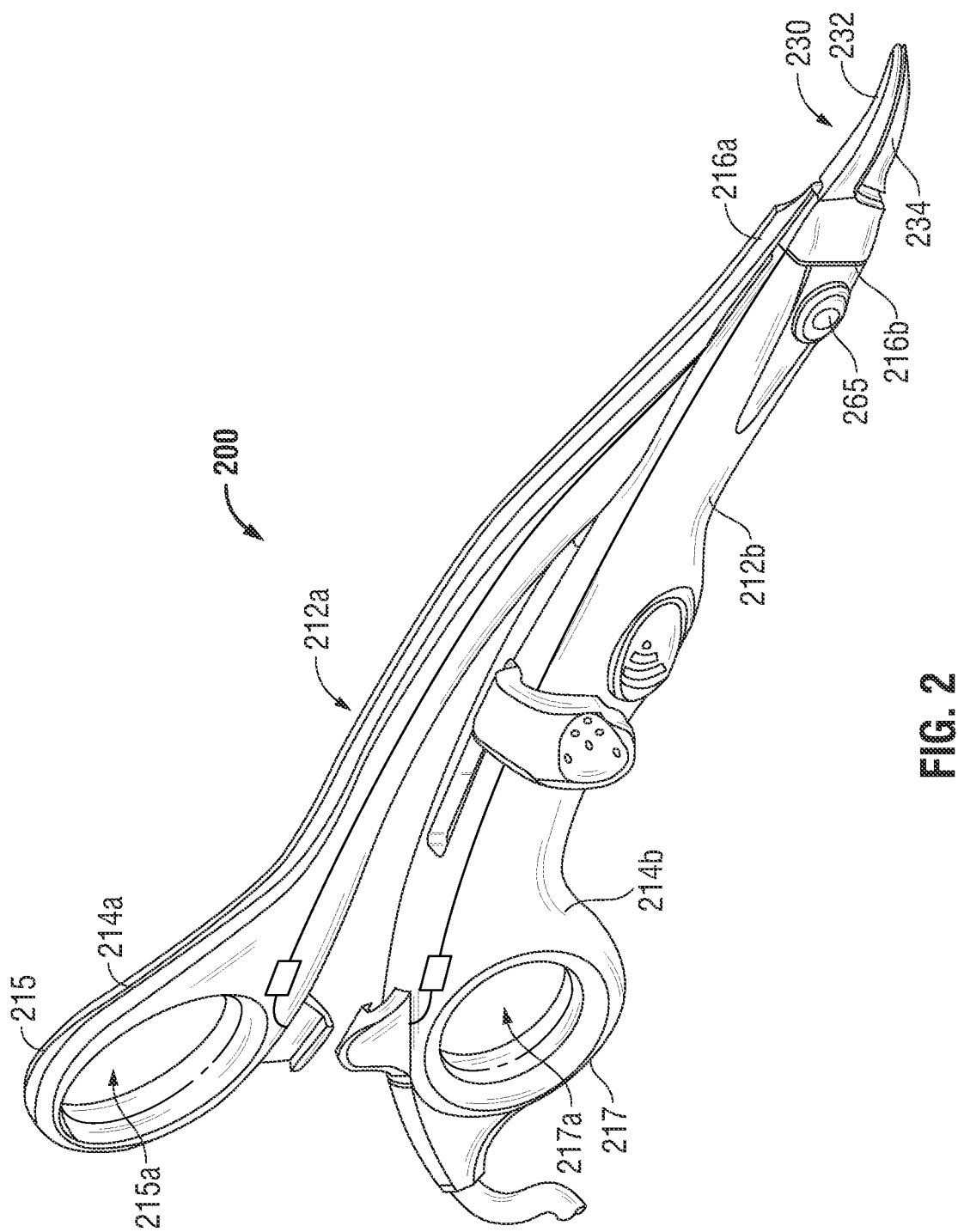
FIG. 2 is a perspective view of an open bipolar forceps in accordance with an embodiment of the present disclosure.

With regard to FIG. 2, an open forceps 200 for use with various surgical procedures is shown. Forceps 200 includes a pair of opposing shafts 212a and 212b having an end effector assembly 230 attached to the distal ends 216a and 216b thereof, respectively. End effector assembly 230 is similar in design to end effector assembly 100 and includes pair of opposing jaw members 232 and 234 that are pivotably connected about a pivot pin 265 and which are movable relative to one another to grasp tissue. Each shaft 212a and 212b includes a handle 215 and 217, respectively, disposed at the proximal end 214a and 214b thereof which each define a finger hole 215a and 217a, respectively, therethrough for receiving a finger of the user. Finger holes 215a and 217a facilitate movement of the shafts 212a and 212b relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

Figure 3A:
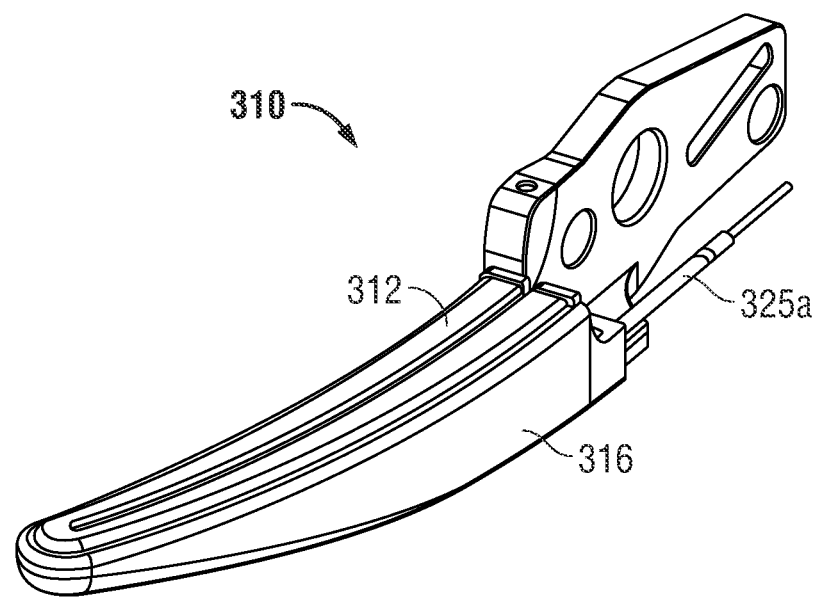
FIGS. 3A and 3B are perspective views of opposing jaw members according to an embodiment of the present disclosure.
Figure 3B:
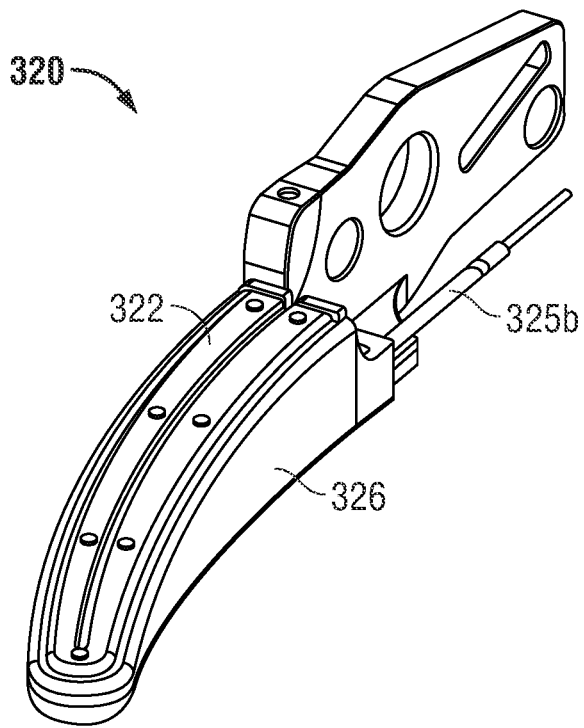

FIGS. 3A and 3B are perspective views of the opposing jaw members 310 and 320. Similar to jaw members 110 and 120, each of the jaw members 310 and 320 include: sealing plates 312 and 322, respectively; electrical jaw leads 325a and 325b, respectively; and support bases 316 and 326 formed as plastic overmolds. Electrical jaw leads 325a and 325b supply energy to at least one of the opposing jaw members 310 and 320.

Figure 4A:
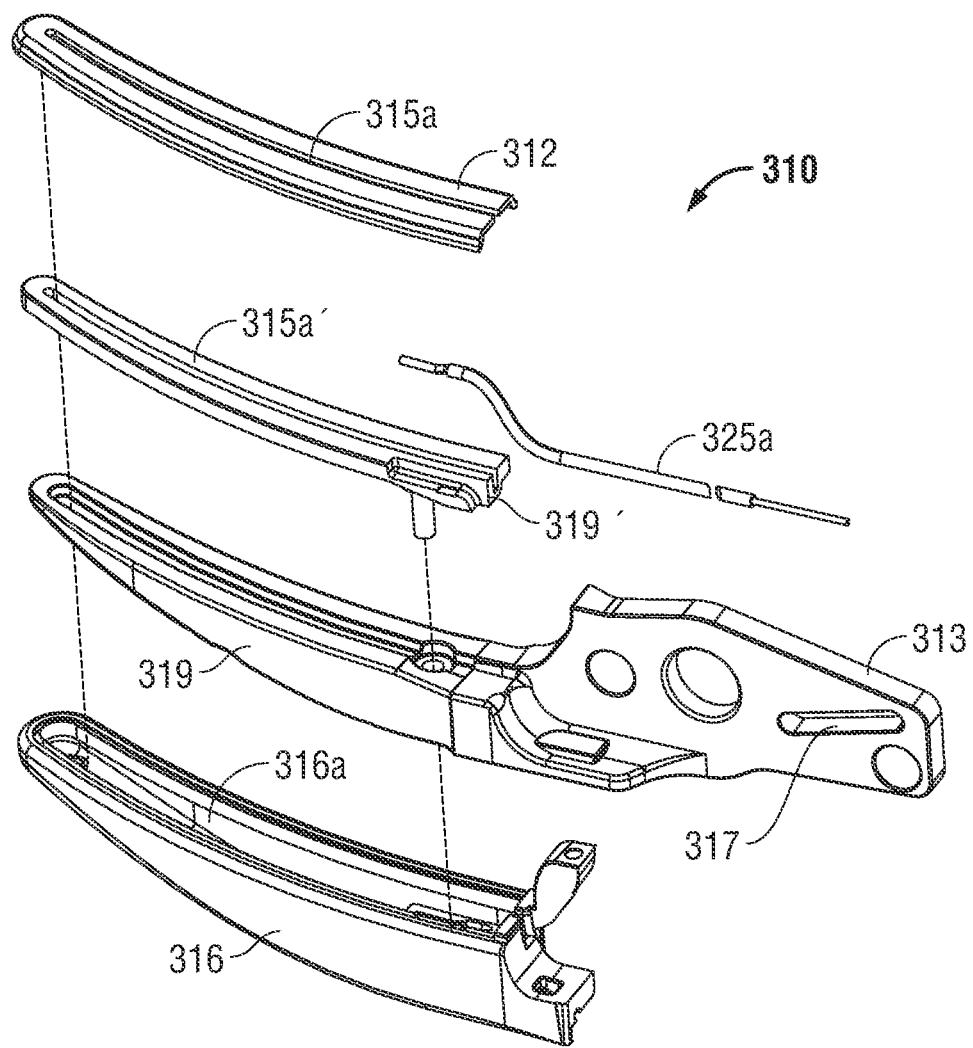
FIGS. 4A and 4B are exploded views of the opposing jaw members of FIGS. 3A and 3B respectively.
Figure 4B:
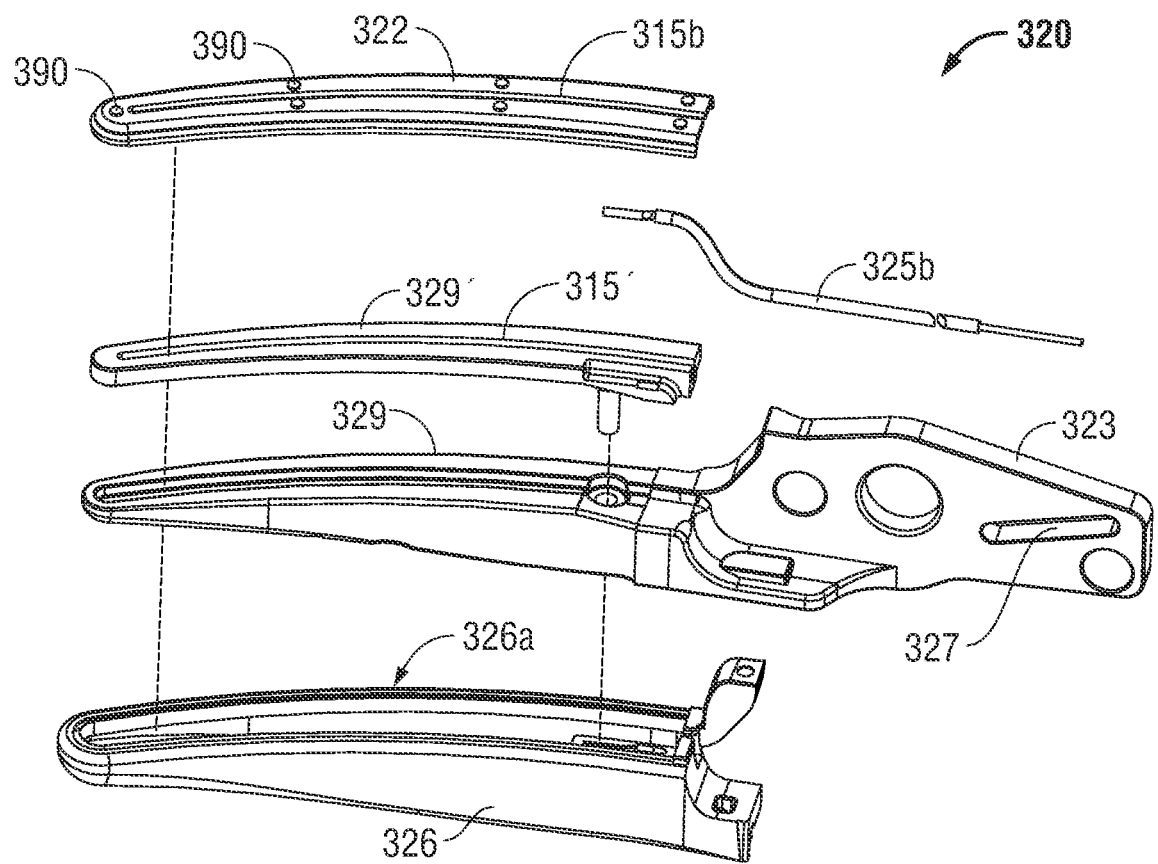

Turning to FIGS. 4A and 4B, the opposing jaw members 310 and 320 include support bases 316 and 326 that each extend distally from flanges 313 and 323, respectively. The support bases 316 and 326 are dimensioned to support insulative plates 319' and 329', which in turn, support electrically conductive sealing plates 312 and 322 thereon. It is contemplated that sealing plates 312 and 322 may be affixed atop the insulative plates 319' and 329', respectively, and support bases 319 and 329, respectively, in any known manner in the art, snap-fit, over-molding, stamping, ultrasonically welded, etc. The support bases 319 and 329, insulative plates 319' and 329', and sealing plates 312 and 322 are encapsulated by the outer insulative housings 316 and 326 by way of a subsequent overmolding process. The jaw members 310 and 320 are connected via an ultrasonic weld to electrical jaw leads 325a and 325b, respectively.

The jaw members 310 and 320 also include proximal flanges 313 and 323 extending proximally from the support bases 319 and 329, respectively, each of which includes an elongated angled cam slot 317 and 327, respectively, defined therethrough. The jaw member 320 also includes a series of piezo electric sensors 390 disposed on the inner facing surface of an electrically conductive sealing plate 312 to define a gap between opposing jaw members 310 and 320 during sealing and cutting of tissue. The series of piezo electric sensors 390 are applied onto the sealing plate 312 during manufacturing. The electrically conductive sealing plates 312 and 322 and the insulative plates 319' and 329' include respective longitudinally-oriented knife slots 315a, 315a' and 315b, 315b', respectively, defined therethrough for reciprocation of the knife blade (not shown).

Figure 5A:
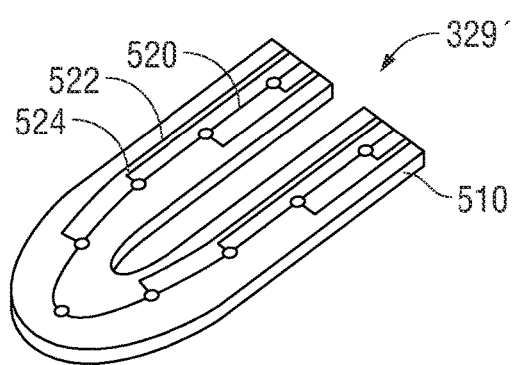
FIG. 5A is a top view of a insulation plate according to an embodiment of the present disclosure.

Turning to FIG. 5A, a top view of insulative plate 329' is shown. Insulative plate 329' is a flex circuit. Flex circuits are used to assemble electronic circuits by mounting electronic devices on flexible plastic substrates. Such plastic substrates may include, but are not limited to, polyimde or polyether ether ketone (PEEK) film. Flex circuits may also be constructed by screen printing silver circuits onto polyester. As shown in FIG. 5A insulative plate 329' has a substrate 510 having circuit traces 520 formed thereon. Circuit traces 520 may be made from copper, silver, or any other electrical conductor. Circuit traces 520 may be formed by any method known to one skilled in the art. For instance, circuit traces 520 may be formed by adhering a conductive layer to substrate 510. Using photolithography, a mask outlining circuit traces 520 may be formed and then the conductive layer may be etched to leave circuit traces 520.

Circuit traces 520 include contacts 524 that may be made from copper, silver or any other electrical conductor. Contacts 524 may be made from the same material as circuit traces 520 or from a material different from circuit traces 520. Each contact 524 is operatively coupled to controller 620 (FIG. 6) via contact traces 522. Contacts 524 and contact traces 522 are formed using the same techniques that may be used to form circuit traces 524. The location of contacts 524 correspond to the location of piezo electric sensors 390. Accordingly, when piezo electric sensors 390 determine a seal pressure, piezo electric sensors 390 provide a signal to controller 620 indicative of the seal pressure via contacts 524 and contact traces 522.

Figure 5B:
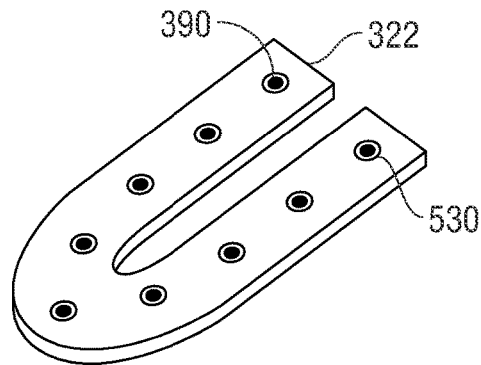
FIG. 5B is a top view of a sealing plate according to an embodiment of the present disclosure.

FIG. 5B depicts a top view of seal plate 322. Seal plate 322 is made from stainless steel, and as described above, has piezo electric sensors 390 disposed therein in locations 530. Seal plate 322 may be formed by any method known to one skilled in the art. For instance, a layer of stainless steel may be provided and shaped to form seal plate 322. Then, a photolithography mask is applied to seal plate 322 leaving locations 530 exposed. An etching solution is applied to seal plate 322 to etch away exposed locations 530. Then the mask is removed leaving seal plate 322 with locations 530 etched away. When jaw member 320 is assembled, piezo electric sensors 390 are placed in locations 530 of seal plate 322 and are coupled to contacts 524 of insulative plate 329'.

Figure 6:
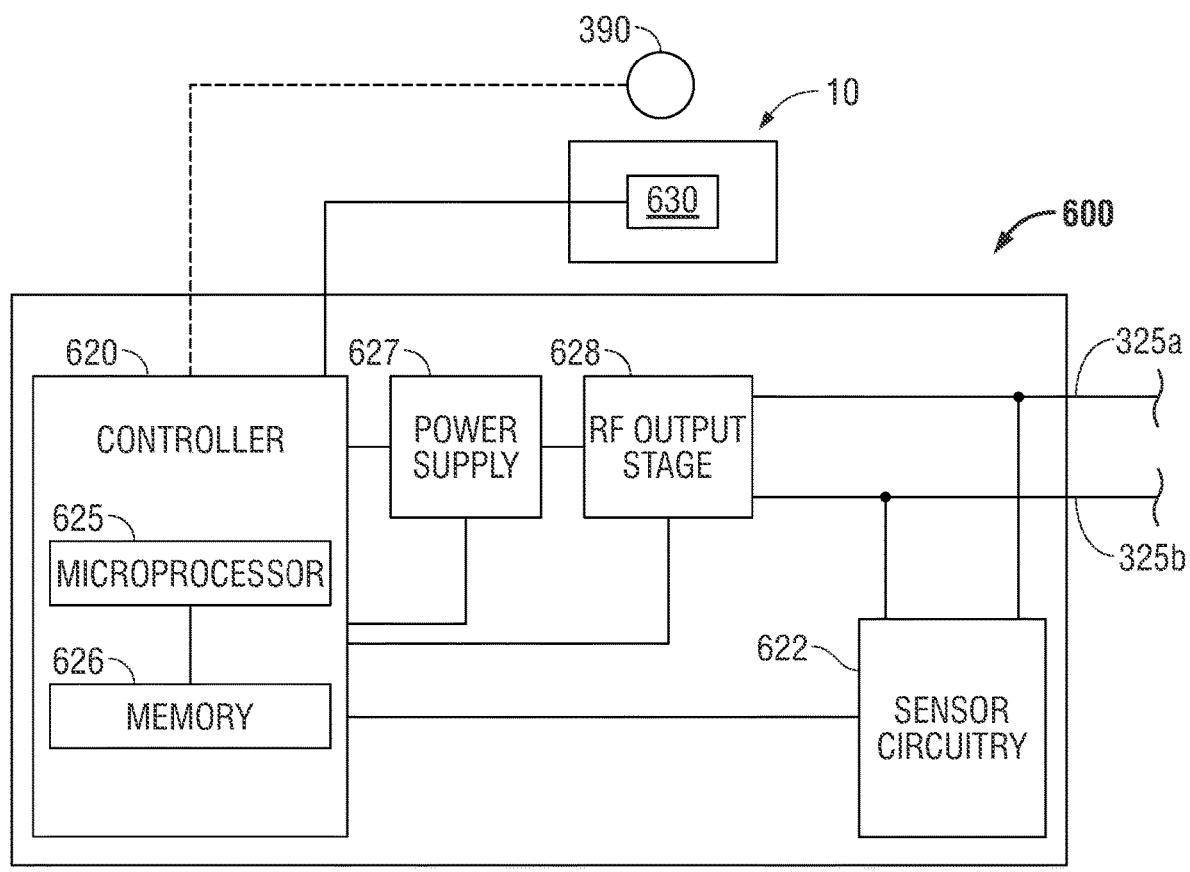
FIG. 6 is a schematic block diagram of an electrosurgical system according to an embodiment of the present disclosure.

FIG. 6 shows a schematic block diagram of the generator 600 having a controller 624, a power supply 627, an RF output stage 628, and a sensor module 622. The power supply 627 provides DC power to the RF output stage 628 which then converts the DC power into RF energy and delivers the RF energy to the instrument 10. The controller 624 includes a microprocessor 625 having a memory 626 which may be volatile type memory (e.g., RAM) and/or non-volatile type memory (e.g., flash media, disk media, etc.). The microprocessor 625 includes an output port connected to the power supply 627 and/or RF output stage 628 that allows the microprocessor 625 to control the output of the generator 600 according to either open and/or closed control loop schemes.

A closed loop control scheme generally includes a feedback control loop wherein the sensor module 622 provides feedback to the controller 24 (i.e., information obtained from one or more sensing mechanisms for sensing various tissue parameters such as tissue impedance, tissue temperature, output current and/or voltage, etc.). The controller 624 then signals the power supply 627 and/or RF output stage 628 which then adjusts the DC and/or RF power supply, respectively. The controller 624 also receives input signals from the input controls of the generator 600 and/or instrument 10. The controller 624 utilizes the input signals to adjust the power output of the generator 600 and/or instructs the generator 20 to perform other control functions.

The microprocessor 625 is capable of executing software instructions for processing data received by the sensor module 622, and for outputting control signals to the generator 600, accordingly. The software instructions, which are executable by the controller 624, are stored in the memory 626 of the controller 624.

The controller 624 may include analog and/or logic circuitry for processing the sensed values and determining the control signals that are sent to the generator 600, rather than, or in combination with, the microprocessor 625.

The sensor module 622 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 624. The sensor module 622 may include control circuitry that receives information from multiple sensors, and provides the information and the source of the information (e.g., the particular sensor providing the information) to the controller 624.

More particularly, the sensor module 622 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

The generator 600 includes suitable input controls (e.g., buttons, activators, switches, touch screen, etc.) for controlling the generator 600, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the instrument 10 may include a plurality of input controls which may be redundant with certain input controls of the generator 600. Placing the input controls at the instrument 10 allows for easier and faster modification of RF energy parameters during the surgical procedure without requiring interaction with the generator 600.

A generator 600 according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Piezo electric sensors 390 are configured to automatically sense various properties of the tissue disposed between the jaw members 110 and 120 and provide feedback to controller 620 during the sealing process. Such properties include, but are not limited to: tissue impedance, tissue type, tissue clarity, tissue compliance, temperature of the tissue or jaw members, and water content in tissue, jaw opening angle, water motality in tissue, energy delivery, and jaw closure pressure. Controller 620 regulates and adjusts the closing pressure between the jaw members 110 and 120 during the sealing process to enhance the tissue seal.

As seen in FIG. 6, piezo electric sensors 390 may be coupled to the control assembly via an open loop or closed loop feedback system to regulate the seal pressure on the tissue between the jaw members 110 and 120. It is important to note that the closure pressure of the jaw members 110 and 120 correlates to, but is not necessarily the same as, the sealing pressure on the tissue disposed between the jaw members 110 and 120. The piezo electric sensors 390 measure the sealing pressure on the tissue and relay the sealing pressure information back to controller 624 which operatively communicates with instrument 10 to adjust the sealing pressure based upon the information provided by piezo electric sensors 390 and the desired sealing pressure according to a predetermined seal pressure profile.

Instrument 10 may include a pressure controller 630 that is operatively coupled to the shaft 12 of the forceps 10. The pressure controller 630 may be any type of electrical, or electro-mechanical mechanism that provides additional force on the drive assembly (not shown) to increase or decrease the closure pressure of the jaw members 110 and 120 which, in turn, increases or decreases the seal pressure on the tissue disposed therebetween. For example, a servo motor, gear assembly, hydraulic mechanism, worm drive, etc. may be coupled to the shaft 12 and operatively coupled to the drive assembly (not shown) to provide additional force to the drive assembly (not shown) as per the information.

As mentioned above, in one embodiment, the initial closure pressure between the jaw members 110 and 120 upon actuation of the handle assembly 30 and locking of the moveable handle 40 relative to the fixed handle 50 is about 3 kg/cm$^2$ to about 16 kg/cm$^2$. The sealing pressure on the tissue may or may not fall within this range. The piezo electric sensors 390 may be configured to initially determine the sealing pressure on tissue prior to initial activation of the forceps. For example, the piezo electric sensors 390 may determine that additional force needs to be provided to the drive assembly (not shown) to increase the closure pressure of the jaw members 110 and 120 which, in turn, increases the sealing pressure of the tissue 400. As mentioned above, the sealing pressure may be determined by tissue impedance, tissue type, tissue clarity, tissue compliance, temperature of the tissue or jaw members, water content in tissue, jaw opening angle, water motality in tissue, energy delivery, etc.

The appropriate sealing pressure for initial activation may be based upon a predetermined pressure profile stored within memory 626, which may be based on tissue type, tissue temperature, tissue size, etc. If more or less sealing pressure on tissue is required, controller 620 communicates with the pressure controller 630 to regulate the closure force of the jaw members 110 and 120. For example, while the handle 40 is locked relative to fixed handle 50, the pressure controller may be configured to provide +/−10 kg/cm$^2$ when required to match a predetermined pressure profile or pressure algorithm.

During the sealing process, the piezo electric sensors 390, controller 624 and the pressure controller 630 all cooperate to regulate the sealing pressure on tissue to conform to a predetermined pressure profile or pressure algorithm. For example, the pressure controller 630 may be instructed by controller 620 to increase the closure pressure on the jaw members 110 and 120 (which increases the sealing pressure on tissue 400) due to the tissue shrinking during the sealing process. Moreover, the seal pressure may be cycled during electrical activation based upon a predetermined sinusoidal pressure profile to enhance the tissue seal. The piezo electric sensors 390 may interact sequentially, simultaneously or in another manner to sense feedback from the tissue and determine the sealing pressure.

The procedure may be automated using a series of piezo electric sensors 390, controller 620 and pressure controller 630. The sealing pressure control system described herein is believed to provide more effective sealing of tissue especially large tissue structures, such as lung tissue. In the automated system, the sealing pressure on the tissue is monitored and adjusted during activation based upon a continually-sensed surgical condition from the sensors relating to any one or more of a series of tissue parameters (e.g., tissue impedance, tissue type, tissue clarity, tissue compliance, temperature of the tissue or jaw members, water content in tissue, jaw opening angle, water motality in tissue, energy delivery, etc.) utilizing an open or closed feed back control loop. The pressure controller 630 may be manual, where the gauge instructs a user through a visual or audible indicator to increase or decrease the closure pressure on the jaw to in turn adjust the sealing pressure on the tissue.

Figure 7:
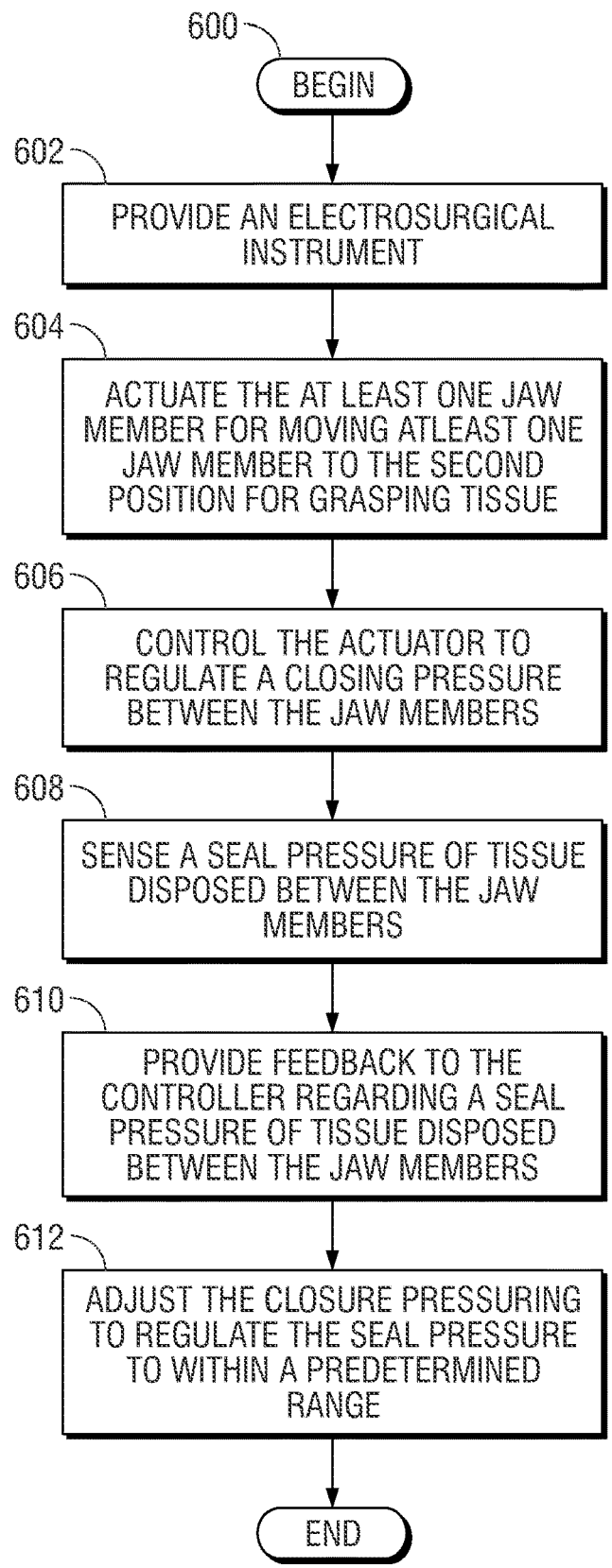
FIG. 7 is a flowchart depicting a sealing method using an electrosurgical instrument.

As shown in FIG. 7, a method for sealing tissue using the forceps 10 is also disclosed herein that includes the initial step 602 of providing an electrosurgical instrument, e.g., forceps 10, including one or more shafts 12 having an end effector assembly 100 at a distal end thereof, the end effector assembly 100 including a pair of opposing jaw members 110 and 120 movable from a first spaced apart position to a second position for grasping tissue. At least one jaw member, e.g., 110 is adapted to connect to an electrical energy source. In step 604, at least one jaw member 110 is actuated to the second position for grasping tissue. The closing pressure between the jaw members is regulated by controlling the actuator in step 606. The instrument 10 senses a seal pressure of tissue 400 disposed between the jaw members 110 and 120 in step 608 and provides feedback to controller 620 regarding the seal pressure of tissue disposed between the jaw members 110 and 120. In step 612, the pressure controller 630 adjusts the closing pressure to regulate the seal pressure of the jaw members 110 and 120 on the tissue during the sealing process to within a predetermined range.

In one method, the seal pressure may be determined prior to initial activation of the forceps, continually-sensed during the sealing process and/or after activation to determine seal quality. The seal pressure may be regulated according to a seal pressure profile (e.g., sinusoidal) or seal pressure algorithm. Moreover, the seal pressure may be cycled during electrical activation based upon a predetermined pressure profile or pressure algorithm.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached figures are presented only to demonstrate certain examples of the disclosure. Other elements, steps, methods and techniques that are insubstantially different from those described above and/or in the appended claims are also intended to be within the scope of the disclosure.

What is claimed is:

1. A method of constructing an end effector assembly, the method comprising:
    forming a first jaw member of the end effector assembly;
    assembling an insulative plate including:
        adhering a conductive layer to a plastic substrate;
        applying a conductive layer mask to the conductive layer such that the conductive layer mask exposes a portion of the conductive layer and outlines a circuit trace;
        etching the exposed portion of the conductive layer;
        removing the conductive layer mask; and attaching the insulative plate to a support base of the first jaw member.

2. The method according to claim 1, wherein the circuit trace includes at least one contact and at least one contact trace.

3. The method according to claim 2, wherein assembling the insulative plate further includes aligning a first sealing plate having a hole defined therein such that the hole overlays the contact of the insulative plate and coupling a sensor to the contact of the insulative plate.

4. The method according to claim 3, further comprising assembling the first sealing plate by applying a sealing plate mask to a stainless steel layer of the first sealing plate to expose a portion of the stainless steel layer.

5. The method according to claim 4, wherein assembling the first sealing plate includes removing the mask.

6. The method according to claim 4, wherein assembling the first sealing plate includes forming the stainless steel layer into the first sealing plate.

7. The method according to claim 3, wherein the sensor is a piezoelectric sensor.

8. The method according to claim 3, wherein the sensor is disposed in the hole of the first sealing plate.

9. The method according to claim 3, wherein a location of the contact corresponds to a location of the sensor.

10. The method according to claim 2, wherein coupling the sensor to the contact of the insulative plate includes raising the sensor relative to the first sealing plate such that the sensor is configured to create a gap between the first and second sealing plates.

11. A method of constructing an end effector assembly, the method comprising:
forming a first jaw member of the end effector assembly;
assembling an insulative plate including:
adhering a conductive layer to a plastic substrate;
applying a conductive layer mask to the conductive layer such that the conductive layer mask exposes a portion of the conductive layer and outlines a circuit trace;
applying an etching solution to the exposed portion of the conductive layer to etch the exposed portion of the conductive layer;
removing the conductive layer mask; and
attaching the insulative plate to a support base of the first jaw member.

12. The method according to claim 11, wherein the circuit trace includes at least one contact and at least one contact trace.

13. The method according to claim 12, wherein assembling the insulative plate further includes aligning a first sealing plate having a hole defined therein such that the hole overlays the contact of the insulative plate and coupling a sensor to the contact of the insulative plate.

14. The method according to claim 13, further comprising assembling the first sealing plate by applying a sealing plate mask to a stainless steel layer of the first sealing plate to expose a portion of the stainless steel layer.

15. The method according to claim 14, wherein assembling the first sealing plate includes removing the mask.

16. The method according to claim 14, wherein assembling the first sealing plate includes forming the stainless steel layer into the first sealing plate.

17. The method according to claim 13, wherein the sensor is a piezoelectric sensor.

18. The method according to claim 13, wherein the sensor is disposed in the hole of the first sealing plate.

19. The method according to claim 13, wherein a location of the contact corresponds to a location of the sensor.

20. The method according to claim 12, wherein coupling the sensor to the contact of the insulative plate includes raising the sensor relative to the first sealing plate such that the sensor is configured to create a gap between the first and second sealing plates.

* * * * *